(12) United States Patent
Zhang et al.

(10) Patent No.: US 12,297,374 B2
(45) Date of Patent: May 13, 2025

(54) COALESCING AGENT FOR AQUEOUS COATING, COALESCING AGENT COMPOSITION AND AQUEOUS COATING

(71) Applicant: Runtai New Material Co., Ltd., Taizhou (CN)

(72) Inventors: Haifei Zhang, Taizhou (CN); Shiyuan Zhang, Taizhou (CN)

(73) Assignee: Runtai New Material Co., Ltd., Jiangsu (CN)

( * ) Notice: Subject to any disclaimer, the term of this patent is extended or adjusted under 35 U.S.C. 154(b) by 751 days.

(21) Appl. No.: 17/543,764

(22) Filed: Dec. 7, 2021

(65) Prior Publication Data
US 2022/0372309 A1 Nov. 24, 2022

(30) Foreign Application Priority Data
Apr. 26, 2021 (CN) .......................... 202110452236.9

(51) Int. Cl.
| | |
|---|---|
| *C09D 7/63* | (2018.01) |
| *C07C 67/03* | (2006.01) |
| *C09D 7/20* | (2018.01) |

(52) U.S. Cl.
CPC .............. *C09D 7/63* (2018.01); *C07C 67/03* (2013.01); *C09D 7/20* (2018.01)

(58) Field of Classification Search
CPC ..... C07C 67/03; C07C 69/732; C08F 236/14; C08K 5/101; C09D 7/63; C09D 7/20; C09D 4/00; C09D 5/024; C09D 125/14
See application file for complete search history.

(56) References Cited

U.S. PATENT DOCUMENTS

2012/0258249 A1* 10/2012 Adamson .............. C07C 69/716
560/182

FOREIGN PATENT DOCUMENTS

WO WO-2012069098 A1 * 5/2012 ............. C08K 5/101

OTHER PUBLICATIONS

Wessel "Biodeterioration of Plastics", Prevention of Deterioration Center, Division of Chemistry and Chemical Technology, National Academy of Sciences—National Research Council, Washington, D. C. 20418, SPE Transactions, Jul. 1964, pp. 193-207. (Year: 1964).*
Eggins et al "Problems of Plastics Deterioration In Building In Tropical Areas", Use of Plasties in the Building Industry (Expert Group fitting), United Nations Industrial Development Organization, Vienna, Sep. 1971. (Year: 1971).*

* cited by examiner

*Primary Examiner* — Anthony J Green
(74) *Attorney, Agent, or Firm* — IPRTOP LLC

(57) ABSTRACT

The present invention provides a coalescing agent for aqueous coatings, a coalescing agent composition, and an aqueous coating. The coalescing agent for aqueous coatings is obtained by esterification reaction of fatty acids and glycol ethers. The coalescing agent prepared by the present invention has a boiling point as high as 330° C., has no irritant odor, and is environmental friendly and safe. It overcomes shortcomings of conventional coalescing agents, which is suitable for various polymer emulsion systems, and can significantly reduce the film-forming temperature of aqueous emulsion coatings and optimize the film-forming performance.

9 Claims, No Drawings

COALESCING AGENT FOR AQUEOUS COATING, COALESCING AGENT COMPOSITION AND AQUEOUS COATING

CROSS REFERENCE TO RELATED APPLICATION

The present application claims the benefit of priority to Chinese Patent Application No. CN 202110452236.9, entitled "COALESCING AGENT FOR AQUEOUS COATING COALESCING AGENT COMPOSITION, AND AQUEOUS COATING", filed with CNIPA on Apr. 26, 2021, the disclosure of which is incorporated herein by reference in its entirety for all purposes.

FIELD OF TECHNOLOGY

The present invention relates to the technical field of coalescing agents for aqueous coatings, in particular to coalescing agents for aqueous coatings, coalescing agent compositions, and aqueous coatings.

BACKGROUND

With the environmental regulations becoming stricter and the environmental awareness growing stronger, more and more aqueous coatings are being used to replace organic solvent coatings for exterior and interior construction, vehicle industry and wood. The polymers in aqueous coatings exist in the form of stable suspended latex particles. When the aqueous coatings are being applied on the surface of substrates, and as the water volatilizes, the distance between the latex particles is continuously reduced, then extrusion deformation occurs, and finally a continuous polymer coating film is formed. If the ambient temperature is lower than the glass transition temperature (Tg) of the polymer in the latex, the polymeric particles will not be able to coalesce and will not be adhered into continuous film, it is necessary to add coalescing agent into aqueous coatings, which can help small polymeric particle dispersed in water to reduce the minimum film-forming temperature (MFFT) of latex and to optimize the performances of the coating film, thereby the performances such as the scrubbing resistance, color development, weather resistance, etc. of the coating film are promoted.

Currently aqueous coatings have compositions of coalescing agents about 0.1% to 10%, which mainly are ether alcohol, alcohol ester, or ester ketone compounds, wherein the compounds are unfavorable in their pungent odor. In addition, alcohol ethers compounds have high volatility and a little of toxicity, which is not beneficial to safety and environmental protection. In addition, some coalescing agents such as ethylene glycol ethers will undergo hydrolysis in latex with high pH, which will seriously affect the performance. Therefore, it is necessary to develop a low odor and low-VOC (volatile organic compounds) coalescing agent, which not only meet predictably stricter future VOC regulatory requirements, but also provide superior film hardness and block and scrub resistance for paints.

SUMMARY

The object of the present invention is to overcome the shortcomings of the prior art, and to provide a coalescing agent for aqueous coatings, a coalescing agent composition and an aqueous coating, so as to solve the problems that coalescing agents in the prior art are not environment-friendly.

To achieve the above object and other relevant objects, the present invention is realized by technical solutions including the followings: In a first aspect, the present invention provides a coalescing agent for aqueous coatings, and the coalescing agent includes a compound of formula I, optionally in combination with varying amounts of a compound of formula II:

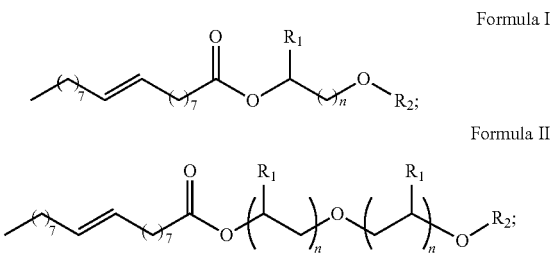

where n is an integer from 1 to 8, $R_1$ independently represents any one of an alkyl with 0 to 4 carbon atoms, an alkenyl with 2 to 4 carbon atoms, an alkynyl with 2 to 4 carbon atoms, a phenyl or a benzyl, and $R_2$ represents an alkenyl with 1 to 4 carbon atoms.

Another aspect of the present invention also provides a coalescing agent for aqueous coatings, and the coalescing agent has a compound with the structure as shown in formula III or a compound with the structure as shown in formula IV:

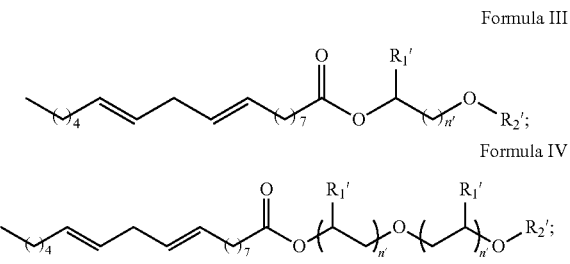

where n' is an integer from 1 to 8, $R_1'$ independently represents any one of an alkyl with 0 to 4 carbon atoms, an alkenyl with 2 to 4 carbon atoms, an alkynyl with 2 to 4 carbon atoms, a phenyl or a benzyl, and $R_2'$ represents an alkenyl with 1 to 4 carbon atoms.

The present invention also provides a coalescing agent composition, and the coalescing agent composition comprises a first coalescing agent and a second coalescing agent, the first coalescing agent are selected from any one of the compounds of formula I or formula II, the second coalescing agent are selected from any one of the compounds of formula III or formula IV, the weight ratio of the first coalescing agent and the second coalescing agent is 1:(0.1-5);

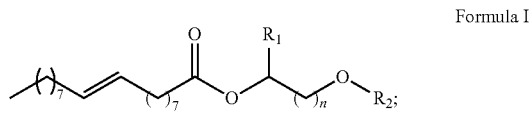

-continued

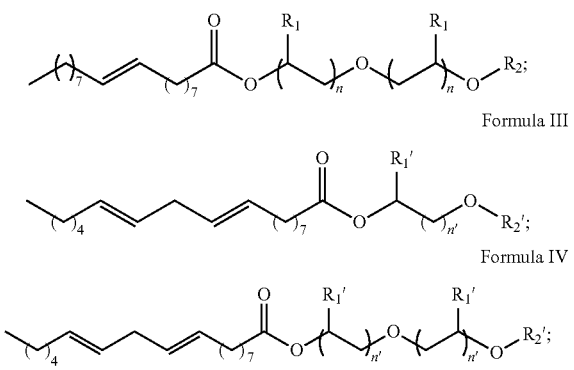

where n or n' is an integer from 1 to 8, $R_1$ or $R_1'$ independently represents any one of an alkyl with 0 to 4 carbon atoms, an alkenyl with 2 to 4 carbon atoms, an alkynyl with 2 to 4 carbon atoms, a phenyl, or a benzyl, and $R_2$ or $R_2'$ represents an alkenyl with 1 to 4 carbon atoms.

Another aspect of the present invention provides a preparation method of a coalescing agent for aqueous coatings, where the method includes the esterification reaction of fatty acids with glycol ethers to obtain the coalescing agent for aqueous coatings, with the structure as shown in formula I, II, III or IV;

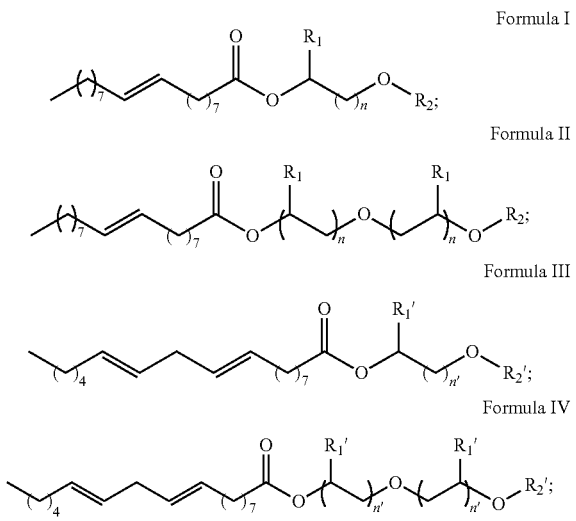

where n or n' is an integer from 1 to 8, $R_1$ or $R_1'$ independently represents any one of an alkyl with 0 to 4 carbon atoms, an alkenyl with 2 to 4 carbon atoms, an alkynyl with 2 to 4 carbon atoms, a phenyl or a benzyl, and $R_2$ or $R_2'$ represents an alkenyl with 1 to 4 carbon atoms.

In one embodiment, the temperature of the esterification reaction is from 100 to 200° C., and the time of the esterification reaction is 12-15 hours.

The present invention also provides an aqueous coating, and the aqueous coating includes an aqueous polymer dispersion and the coalescing agent composition as described above. The weight fraction of the coalescing agent composition is in the range from 1% to 30%, with the solid content amount of the aqueous coating being 100% by weight.

In one embodiment, the aqueous polymer dispersion has a glass transition temperature of from 5° C. to 10° C.

In one embodiment, the polymer dispersion is one or more of an acrylic acid copolymer and a styrene-acrylic acid copolymer.

In one embodiment, the weight fraction of the aqueous polymer dispersion is in the range from 10% to 80%, with the solid content amount of the aqueous coating being 100% by weight.

Finally, the present invention also provides a method of coating, including: forming the aqueous coating as described above; applying the aqueous coating to a substrate; and drying the applied aqueous coating or allowing the applied aqueous coating to dry.

As mentioned above, the main advantages of the present invention include: the coalescing agent prepared by the present invention has a boiling point as high as 330° C., has no irritant odor, and is environmental friendly and safe. It overcomes shortcomings of alcohol-ether coalescing agents, for example, they are not environmentally friendly. The coalescing agent prepared by the present invention is suitable for various polymer emulsion systems, and can significantly reduce the film-forming temperature for aqueous emulsion coatings and optimize the film-forming performance.

The coalescing agent prepared by the present invention is obtained on the basis of the research on the film-forming mechanism of aqueous emulsion coatings. Alcohol ketone ester compounds and diacid ester compounds have no negative effect on human health, and the boiling points thereof are higher than 250° C., which means that they are non-VOC products. The insolubility of the coalescing agent in water can avoid the loss of the coalescing agent by water evaporation. The coalescing agent has good compatibility with many kinds of polymer emulsion system, and will not easily be hydrolyzed in emulsion systems. The coalescing agent prepared by the present invention can not only reduce the MMFT of the coating, but also effectively optimize the film-forming performance of the coating, and optimize the gloss, weather resistance, and other properties of the coating film.

It is easier to understand the above and other features, aspects and advantages of this application with reference to the following detailed description.

DETAILED DESCRIPTION

Embodiments of the present invention will be described below with specific examples, and those skilled in the art can easily understand other advantages and effects of the present invention from the disclosure in the specification. The present invention can also be carried out or applied in other different specific embodiments, and various modifications or changes may also be made to the details in the specification based on different ideas and applications without departing from the spirit of the present disclosure.

The present invention first provides a coalescing agent for aqueous coatings. The coalescing agent is from a fatty acid glycol ether ester, and the coalescing agent can be obtained by esterification reaction of glycol ether and oleic acid, and the coalescing agent has the structure as shown in formula I or the structure as shown in formula II:

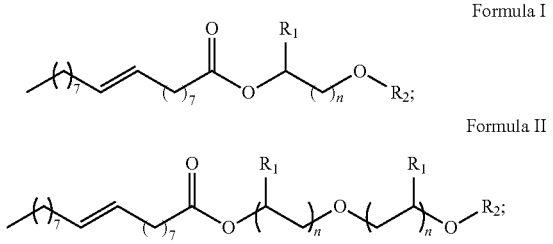

Formula I

Formula II where n can be an integer from 1 to 8, for example, n can be 2, 3, 4, 5, 6, or 7, and $R_1$ independently represents any one of an alkyl with 0 to 4 carbon atoms (for example, an alkyl with 0, 1, 2, or 3 carbon atoms), an alkenyl with 2 to 4 carbon atoms (for example, an alkene with 3 carbon atoms), an alkynyl with 2 to 4 carbon atoms (for example, an alkynyl with 3 carbon atoms), a phenyl, and a benzyl, and $R_2$ represents an alkenyl with 1 to 4 carbon atoms (for example, the number of carbon atoms is 2 or 3).

The present invention also provides another coalescing agent. The coalescing agent has the structure as shown in formula III or formula IV, which can be obtained by esterification reaction of glycol ether and linoleic acid.

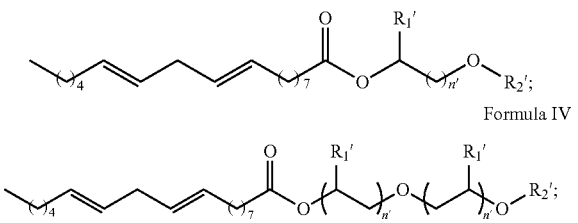

Formula III

Formula IV where n' can be an integer from 1 to 8, for example, n' can be 2, 3, 4, 5, 6, or 7, and $R_1'$ can independently represent any one of an alkyl with 0 to 4 carbon atoms, for example, an alkyl with 0, 1, 2, or 3 carbon atoms, an alkenyl with 2-4 carbon atoms, for example, an alkene with 3 carbon atoms, or an alkynyl with 2-4 carbon atoms, for example, an alkynyl with 3 carbon atoms, a phenyl or a benzyl; and $R_2'$ represents an alkenyl with 1 to 4 carbon atoms, for example, the number of carbon atoms is 2 or 3.

Another aspect of the present invention also provides a coalescing agent composition, wherein the coalescing agent composition can include a first coalescing agent and a second coalescing agent, the first coalescing agent can be selected from any one of the compounds with the structure shown in formula I and the structure shown in formula II, the second coalescing agent can be selected from any one of the compounds with the structure shown in formula III and the structure shown in formula IV, and the coalescing agent composition can be obtained by mixing the first coalescing agent and the second coalescing agent through stirring. The weight ratio of the first coalescing agent and the second coalescing agent is 1:(0.1-5), such as 1:0.2, 1:0.5, 1:2, 1:3, etc., and further preferably, it can be 1:2. The coalescing agent composition of the present invention can be used in the preparation of aqueous coatings, and the coalescing agent can be added in the production process of aqueous coatings.

The present invention also provides a preparation method of the coalescing agent as described above, where the method includes esterification reaction of fatty acid with glycol ether to obtain coalescing agent for aqueous coatings, with the structure as shown in formula I, II, III or IV. In some embodiments, the fatty acid can be either oleic acid or linoleic acid, and the glycol ether have the structure as follows:

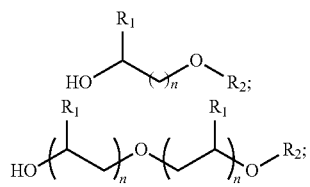

where n can be an integer from 1 to 8, for example, n can be 2, 3, 4, 5, 6, 7, and $R_1$ can independently represent any one of an alkyl with 0-4 carbon atoms, for example, an alkyl with of 0, 1, 2, or 3 carbon atoms, an alkenyl with 2-4 carbon atoms, for example, an alkene with 3 carbon atoms, an alkynyl with 2-4 carbon atoms, for example, an alkynyl with 3 carbon atoms, a phenyl and a benzy; and $R_2$ can represent an alkenyl with 1-4 carbon atoms, for example, the number of carbon atoms is 2 or 3.

The esterification reaction can be carried out under catalytic conditions. The catalyst may be p-toluenesulfonic acid. The amount of the catalyst may be 0.5%-1% of the fatty acid by weight. The reaction temperature may be 100° C.-200° C. The esterification reaction time may be 12-15 hours. After the esterification reaction, extraction can be performed by dichloromethane. And the coalescing agent can be obtained by vacuum distillation.

Another aspect of the present invention also provides an aqueous coating, wherein the aqueous coating includes an aqueous polymer dispersion and the coalescing agent composition, and the weight fraction of the coalescing agent composition is in the range from 1% to 30%, with the solid content of the aqueous coating amount being 100% by weight. In some embodiments, the amount of the coalescing agent is in the range from 1% to 15% by weight, preferable is 1%-12% by weight, such as 4%, 5%, 6%, 7%, 8%, 10%, etc., the present invention can ensure that the film has a certain degree of transparency by controlling the percentage of the coalescing agent in the coating. In some embodiments, the weight fraction of the aqueous polymer dispersion can be in the range from 10 to 80%, with the solid content amount of the aqueous coating being 100% by weight, and further preferably the weight fraction of the aqueous polymer dispersion can be 45%-75%, such as 50%, 60%, 65%, etc. The raw material of the aqueous coating polymer dispersion can be one or more of acrylic acid copolymer and styrene-acrylic acid copolymer.

The aqueous coating may also include pigment, additives, and solvent. The pigment may include one or more of titanium dioxide, such as anatase and rutile titanium dioxide, zinc oxide, antimony oxide, iron oxide, magnesium silicate, calcium carbonate, aluminum silicate, silica, and various clays such as kaolin and coated clay. The additives may include but are not limited one or more of a pigment increment agent, colorant, surfactant, rheological modifier, texture agent, defoamer, fungicide, wetting agent, dispersant, crosslinking agent, thickener, antifreeze, stabilizer, etc.

In some embodiments, in order to increase the solid content of the aqueous coating, the aqueous coating further includes other coalescing agents, which don't volatilize when the coating is dried, and then form a part of the film. The other coalescing agents can be one or more of benzoate ester, ester-alcohol, ethylene glycol-ether, long-chain aliphatic alcohol, and aromatic alcohol. The solvent may be water.

The aqueous coating of the present invention can provide the polymer dispersion of the present invention with a lower glass transition temperature due to the addition of the coalescing agent composition as described above. In some embodiments, the polymer dispersion of the present invention has a lower glass transition temperature, which can be 0-15° C., and further preferably, the lower glass transition temperature can be 5-10° C., such as 6° C., 7° C., 8° C., 9° C.

The present invention also provides a method of forming a coating, and the method includes: forming the aqueous coating as described above; applying the aqueous coating to a substrate; and drying the applied aqueous coating to form a film. In some embodiments, the aqueous coating can be coated to a substrate, and the polymer dispersion in the aqueous coating can form a film coating on the substrate after drying or baking. The aqueous coating of the present invention can be applied to substrates, such as wood substrates, metal substrates, plastic substrates, marine substrates, civil engineering substrates, cement-based substrates, etc., furthermore, the aqueous coating of the present invention can be an aqueous coating for construction. The aqueous coating can be applied to a substrate by conventional coating methods, such as brushes, rollers, curtain coaters and spraying methods, as well as air-atomized spraying, air-assisted spraying, airless spraying, high-volume and low-pressure spraying and air-assisted airless spraying, etc. The aqueous coating can be prepared by a technique well known in the field of coatings.

It is to be noted that, unless otherwise specified, "%" and "portion" shown herein refer to "% by weight" and "portion by weight", respectively.

Hereinafter, the present invention will be explained more specifically by citing examples, which should not be understood as limiting. Within the scope consistent with the spirit of the present invention, appropriate modifications can be made, which fall into the technical scope of the present invention.

(1) Preparation of Ethylene Glycol Methyl Ether Oleate (OA-1) Coalescing Agent

In the preparation of the coalescing agent OA-1, 1.0 mol oleic acid and 1.1 mols ethylene glycol methyl ether and 100 g toluene were added into round-bottom flask, and p-toluene sulfonic acid (1% by weight of oleic acid) was used as a catalyst for refluxing at 110° C. for 12 h. Then, the solvent in the system was evaporated and extracted with dichloromethane. After extraction, sodium bicarbonate was added to the product. Then, the dichloromethane layer was evaporated to obtain OA-1, and the chemical reaction formula of this example is shown below.

(2) Preparation of Propylene Glycol Methyl Ether Oleate (OA-2) Coalescing Agent

The coalescing agent OA-2 can be prepared by the same method as the preparation of OA-1, but in the first step, propylene glycol methyl ether is used instead of ethylene glycol methyl ether.

(3) Preparation of Butylene Glycol Methyl Ether Oleate (OA-3) Coalescing Agent

The coalescing agent OA-3 can be prepared by the same method as the preparation of OA-1, but in the first step, butylene glycol methyl ether is used instead of ethylene glycol methyl ether.

(4) Preparation of Diethylene Glycol Ethyl Ether Oleate (OA-4) Coalescing Agent

The coalescing agent OA-4 can be prepared by the same method as the preparation of OA-1, but in the first step, diethylene glycol ethyl ether is used instead of ethylene glycol methyl ether.

(5) Preparation of Dipropylene Glycol Ethyl Ether Oleate (OA-5) Coalescing Agent The coalescing agent OA-5 can be prepared by the same method as the preparation of OA-1, but in the first step, dipropylene glycol ethyl ether is used instead of ethylene glycol methyl ether.

(6) Preparation of Ethylene Glycol Methyl Ether Linoleate (LA-1) Coalescing Agent In the preparation of the coalescing agent LA-1, 1.0 mol of linoleic acid and 1.1 mols of ethylene glycol methyl ether and 100 g toluene were added into a round-bottom flask, and refluxed at 110° C. for 12 hours with using hydroquinone as a polymerization inhibitor and using p-toluene sulfonic acid (1% by weight of linoleic acid) as a catalyst. Then, the solvent in the system was evaporated and extracted with dichloromethane. After extraction, sodium bicarbonate was added to the product. Then, the dichloromethane layer was evaporated to obtain the LA-1 product, whose properties were further analyzed. The chemical reaction formula of this example is shown below.

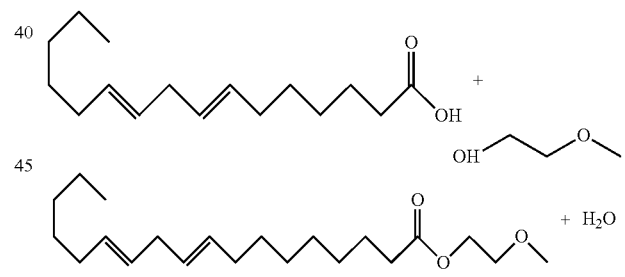

(7) Preparation of Propylene Glycol Methyl Ether Linoleate (LA-2) Coalescing Agent The coalescing agent LA-2 can be prepared by the same method as the preparation of LA-1, but in the first step, propylene glycol methyl ether is used instead of ethylene glycol methyl ether.

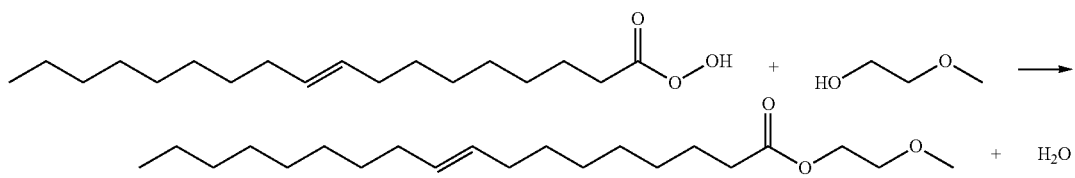

(8) Preparation of Butylene Glycol Methyl Ether Linoleate (LA-3) Coalescing Agent The coalescing agent LA-3 can be prepared by the same method as the preparation of LA-1, but in the first step, butylene glycol methyl ether is used instead of ethylene glycol methyl ether.

(9) Preparation of Diethylene Glycol Ethyl Ether Linoleate (LA-4) Coalescing Agent The coalescing agent LA-4 can be prepared by the same method as the preparation of LA-1, but in the first step, diethylene glycol ethyl ether is used instead of ethylene glycol methyl ether.

(10) Preparation of Dipropylene Glycol Ethyl Ether Linoleate (LA-5) Coalescing Agent The coalescing agent LA-5 can be prepared by the same method as the preparation of LA-1, but in the first step, dipropylene glycol ethyl ether is used instead of ethylene glycol methyl ether.

Performance Test of Fatty Acid Glycol Ether Ester Coalescing Agent

Film-Forming Effect

Compared with the commercially available coalescing agent Texanol™, the film-forming effect of the coalescing agent OA-1 to LA-5 can be tested according to the following steps.

1. 20 g polymer emulsion (acrylic acid copolymer or styrene-acrylic acid copolymer) were added to a test beaker.
2. A certain amount of the coalescing agent was slowly added during a stirring process until the coalescing agent and binder are evenly mixed.
3. The coalescing agent and binder prepared by step 2 on were stretched on supporting paper by a wire coater until a film layer with a thickness of 100 microns is obtained. The film is then dried at room temperature.
4. The appearance of the film after drying was observed, and the film is required to be transparent and undamaged.

Drying Performance

Compared with the commercially available coalescing agent Texanol™, the drying performance of the coalescing agent OA-1 to LA-5 can be tested according to the following steps:

1. 20 g polymer emulsion selected from acrylic acid copolymer or styrene-acrylic acid copolymer and a certain proportion of coalescing agent were added to a test beaker, then the mixture were evenly mixed.
2. The mixture of the coalescing agent and binder prepared at step 1 were stretched on supporting paper by a wire coater until a film layer is obtained with a thickness of 100 microns. The film is then dried at room temperature.
3. The prepared film were touched with a finger, and the time were recorded when the resulted fingerprint disappeared from the film.

Glass Transition Temperature

The dried film was tested for glass transition temperature by differential scanning calorimetry (DSC) according to the method of GB/T19466.2-2004.

Odor Test

Compared with the commercially available coalescing agent Texanol™, the odor test of the coalescing agent OA-1 to LA-5 can be carried out according to the following steps.

1. 10 g polymer emulsion mixed with different coalescing agent was added to test beakers respectively.
2. Five evaluators were asked to test the odor and record the intensity of the odor as from 0 to 3, where 3 indicates the strongest odor intensity and 0 indicates no odor was detected.

The performance evaluation table of the present invention is shown in Table 1. The ratio of coalescing agents added in Table 1 is 5%. In Table 1, PE represents the polymer emulsion without any coalescing agent, PE(Texanol™) represents the polymer emulsion with commercially available coalescing agent Texanol added, PE(OA-1) represents the polymer emulsion with only OA-1 coalescing agent added, and PE [OA-1+LA-1(1:0.1)] represents the polymer emulsion with OA-1 and LA-1 coalescing agent added at a weight ratio of 1:0.1, and so on.

TABLE 1

Performance evaluation table

| Coating type | Tg (° C.) | Film-forming effect | Odor | Drying time (hour) |
|---|---|---|---|---|
| PE | 22.5 | translucent | 3 | 23 |
| PE (Texanol™) | 13.2 | transparent | 3 | 18 |
| PE (OA-1) | 15.4 | opaque | 1 | 40 |
| PE (OA-2) | 14.1 | opaque | 1 | 45 |
| PE (OA-3) | 12.7 | opaque | 1 | 48 |
| PE (OA-4) | 15 | opaque | 1 | 52 |
| PE (OA-5) | 11.6 | opaque | 1 | 58 |
| PE (LA-1) | 12.6 | translucent | 1 | 25 |
| PE (LA-2) | 10.6 | translucent | 1 | 27 |
| PE (LA-3) | 8.2 | translucent | 2 | 36 |
| PE (LA-4) | 12.2 | translucent | 2 | 40 |
| PE (LA-5) | 11.1 | translucent | 2 | 44 |
| PE 〖OA-1 + LA-1(1:0.1)〗 | 9.9 | opaque | 2 | 36 |
| PE 〖OA-2 + LA-2(1:0.1)〗 | 10.6 | opaque | 2 | 29 |
| PE 〖OA-3 + LA-3(1:0.1)〗 | 14.1 | opaque | 2 | 31 |
| PE 〖OA-4 + LA-4(1:0.1)〗 | 15.8 | opaque | 2 | 39 |
| PE 〖OA-5 + LA-5(1:0.1)〗 | 13.5 | opaque | 2 | 41 |
| PE 〖OA-1 + LA-1(1:0.5)〗 | 6.7 | opaque | 2 | 22 |
| PE 〖OA-2 + LA-2(1:0.5)〗 | 4.6 | opaque | 2 | 27 |
| PE 〖OA-3 + LA-3(1:0.5)〗 | 8 | opaque | 2 | 29 |
| PE 〖OA-4 + LA-4(1:0.5)〗 | 10.8 | opaque | 2 | 35 |
| PE 〖OA-5 + LA-5(1:0.5)〗 | 10.5 | opaque | 2 | 37 |
| PE 〖OA-1 + LA-1(1:1)〗 | 15.7 | opaque | 1 | 20 |
| PE 〖OA-2 + LA-2(1:1)〗 | 14.6 | translucent | 1 | 23 |
| PE 〖OA-3 + LA-3(1:1)〗 | 13 | translucent | 1 | 28 |
| PE 〖OA-4 + LA-4(1:1)〗 | 14.8 | translucent | 1 | 31 |
| PE 〖OA-5 + LA-5(1:1)〗 | 12.5 | translucent | 1 | 33 |
| PE 〖OA-1 + LA-1(1:2)〗 | 16.7 | transparent | 1 | 17 |
| PE 〖OA-2 + LA-2(1:2)〗 | 15.8 | transparent | 1 | 21 |
| PE 〖OA-3 + LA-3(1:2)〗 | 16 | transparent | 1 | 26 |
| PE 〖OA-4 + LA-4(1:2)〗 | 16.8 | transparent | 1 | 28 |
| PE 〖OA-5 + LA-5(1:2)〗 | 15.3 | transparent | 1 | 29 |
| PE 〖OA-1 + LA-1(1:5)〗 | 7.7 | transparent | 1 | 30 |
| PE 〖OA-2 + LA-2(1:5)〗 | 6.6 | transparent | 1 | 33 |
| PE 〖OA-3 + LA-3(1:5)〗 | 9 | transparent | 1 | 38 |
| PE 〖OA-4 + LA-4(1:5)〗 | 10.8 | transparent | 1 | 41 |
| PE 〖OA-5 + LA-5(1:5)〗 | 10.5 | transparent | 1 | 39 |

It can be seen from Table 1 that the effect of adding the two different coalescing agents synthesized by oleic acid and linoleic acid into the polymer emulsion is better than that of adding one alone. The mixed coalescing agent composition show obvious advantages in low film-forming temperature and film-forming effect, and the resulted film is also better. This is because oleic acid is generally better than oleic acid in reducing the film-forming temperature, but oleic acid has shortcomings such as re-sticking, long drying time, and poor film transparency, linoleic acid can just make up for shortcomings and has strong adhesion.

Therefore, the present invention effectively overcomes various shortcomings in the prior art and thus has a high value for industrial application. The above-mentioned embodiments only exemplarily illustrate the principles and effects of the present invention, and are not used to limit the present invention. Anyone skilled in the art can modify or change the above-mentioned embodiments without departing from the spirit and scope of the present invention. Therefore, all equivalent modifications or changes made by those skilled in the art without departing from the spirit and technical ideas disclosed in the present invention should still be covered by the claims of the present invention.

What is claimed is:

1. A coalescing agent for aqueous coating, wherein the coalescing agent has the structure as shown in formula III or the structure as shown in formula IV:

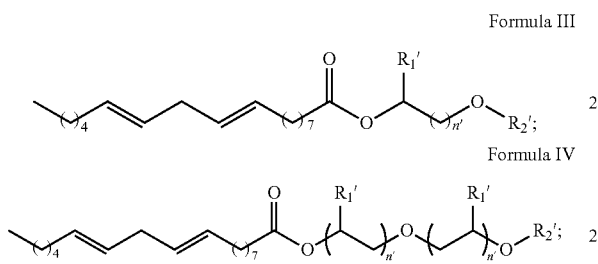

where n' is an integer from 1 to 8, $R_1'$ independently represents any one of an alkyl with 0 to 4 carbon atoms, an alkenyl with 2 to 4 carbon atoms, an alkynyl with 2 to 4 carbon atoms, a phenyl or a benzyl, and $R_2'$ represents an alkenyl with 1 to 4 carbon atoms.

2. A coalescing agent composition, wherein the coalescing agent composition comprises a first coalescing agent and a second coalescing agent, the first coalescing agent is selected from any one of the compounds with the structure shown in formula I or the structure shown in formula II, the second coalescing agent is the coalescing agent according to claim 1, the weight ratio of the first coalescing agent and the second coalescing agent is 1:(0.1-5);

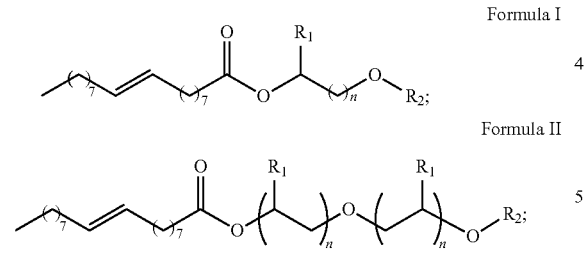

where n is an integer from 1 to 8, $R_1$ independently represents any one of an alkyl with 0 to 4 carbon atoms, an alkenyl with 2 to 4 carbon atoms, an alkynyl with 2 to 4 carbon atoms, a phenyl, or a benzyl, and $R_2$ represents an alkenyl with 1 to 4 carbon atoms.

3. A preparation method of a coalescing agent for aqueous coatings, wherein the method comprises esterification reaction of fatty acids with glycol ethers to obtain the coalescing agent for aqueous coatings, with structure shown in formula I, II, III or IV;

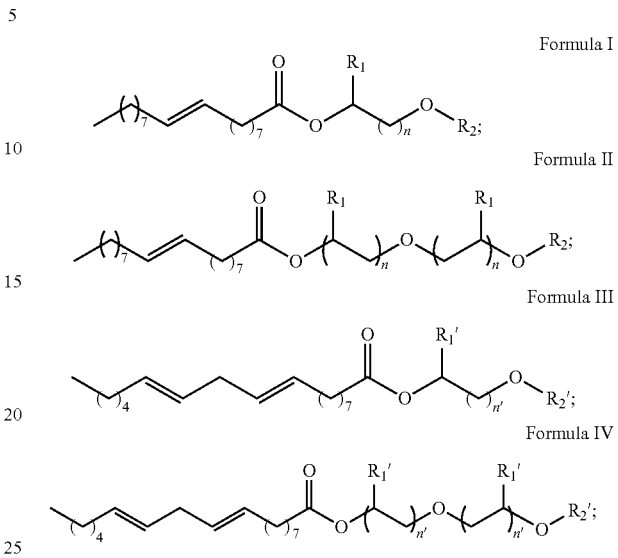

where n or n' is an integer from 1 to 8, R1 or R1' independently represents any one of an alkyl with 0 to 4 carbon atoms, an alkenyl with 2 to 4 carbon atoms, an alkynyl with 2 to 4 carbon atoms, a phenyl or a benzyl, and R2 or R2' represents an alkenyl with 1 to 4 carbon atoms.

4. The method according to claim 3, wherein the temperature of the esterification reaction is from 100 to 200° C., and the time of the esterification reaction is from 12 to 15 hours.

5. An coating composition, wherein the coating composition comprises an aqueous polymer dispersion and the coalescing agent composition according to claim 2, and the weight fraction of the coalescing agent composition is in the range from 1% to 30%, with the solid content amount of the coating composition being 100% by weight.

6. The coating composition according to claim 5, wherein the aqueous polymer dispersion has a glass transition temperature of from 5° C. to 10° C.

7. The coating composition according to claim 5, wherein the polymer dispersion is one or more of an acrylic acid copolymer and a styrene-acrylic acid copolymer.

8. The coating composition according to claim 5, wherein the weight fraction of the aqueous polymer dispersion is in the range from 10% to 80%, with the solid content amount of the coating composition being 100% by weight.

9. A method of coating, comprising:
forming the coating composition according to claim 5;
applying the coating composition to a substrate; and
drying the applied coating composition or allowing the applied coating composition to dry.

* * * * *